US00PP33655P2

(12) United States Plant Patent
Zemzami

(10) Patent No.: US PP33,655 P2
(45) Date of Patent: Nov. 23, 2021

(54) MANDARIN TREE NAMED 'STAR COTT 3'

(50) Latin Name: *Citrus reticulata*
Varietal Denomination: Star Cott 3

(71) Applicant: Qualiagro SA, Casablanca (MA)

(72) Inventor: Mustapha Zemzami, Kenitra (MA)

(73) Assignee: Qualiagro SA, Casablanca (MA)

( * ) Notice: Subject to any disclaimer, the term of this patent is extended or adjusted under 35 U.S.C. 154(b) by 0 days.

(21) Appl. No.: 17/031,439

(22) Filed: Sep. 24, 2020

(51) Int. Cl.
*A01H 5/08* (2018.01)
*A01H 6/78* (2018.01)

(52) U.S. Cl.
USPC ..... Plt./201

(58) Field of Classification Search
USPC ..... Plt./156, 202, 201
See application file for complete search history.

(56) References Cited

PUBLICATIONS

Bulletin de la Protection des Obtentions Vegetales. 2017. http://www.onssa.gov.ma/images/controle_semences/bulletin-de-protection-des-obtentions-vegetales-n28-septembre-2017.pdf. 12 pages. (Year: 2017).*

* cited by examiner

*Primary Examiner* — Susan McCormick Ewoldt
*Assistant Examiner* — Karen M Redden
(74) *Attorney, Agent, or Firm* — Klarquist Sparkman, LLP

(57) ABSTRACT

A new and distinct mandarin tree characterized by low viable pollen, female sterility allowing production of seedless fruits, later maturity and compact canopy with significant potential for high density planting and swift achievement of significant yield in a short time.

7 Drawing Sheets

Genus and species: *Citrus reticulata.*
Variety denomination: 'Star Cott 3'.

CROSS-REFERENCE TO RELATED APPLICATIONS

Co-pending U.S. application Ser. No. 17/031,295 (Mandarin Tree named 'Star Cott 1') was developed by the same breeding program.

ORIGIN OF THE INVENTION

The present invention relates to a new and distinct variety of a mandarin tree named 'Star Cott 3', which was originated by the inventor by gamma irradiating the variety 'Nadorcott' (U.S. Plant Pat. No. 10,480), and selecting for trees having pronounced male and female sterility and desired maturity timeframe in the season.

BACKGROUND OF THE INVENTION

The *Citrus* industry is facing tremendous challenges to cope with the recent extensive world-wide plantings of soft *Citrus*. This congested the market supply due to the narrow maturity windows of conventional varieties, especially clementine varieties, which suffer unprofitable sell prices that impact tremendously farmer's income. Mandarins provide a solution as a soft easy peeling *Citrus* fruit. However, the late maturity of mandarins does not offer possibilities to fill the gap of the supply shortage of mid-season in the market from end November to end January. Furthermore, mandarins cause problems of cross-pollination, which are unacceptable to farmers, and fruit seediness, which constitutes a major constraint to access better rewarding markets.

To overcome this problem, a breeding program was instituted to generate new varieties of non-cross-pollinating mandarins that can fill the gap of mid-season market supply with seedless easy peeler *Citrus* fruits. The breeding program targeted creation of new varieties with both male and female sterility with a range of maturity windows that are better adapted to the market. Budwood of 'Nadorcott' (U.S. Plant Pat. No. 10,480) was gamma irradiated in 2013 using a Cobal-60 panoramic irradiator in Boukhalef, Tangier, Morocco.

Irradiated bud wood was sequentially grafted in Kenitra, Morocco on Volkamer lemon root-stock (unpatented) to speed up growth. The last generation of vegetatively propagated plants was planted in 2015 at an experimental field in Beni Mellal, Morocco. Selection observations started in 2017 with a focus on pronounced male and female sterility, adequate maturity period in the late season, yield potential and other agronomic features of interest.

BRIEF SUMMARY OF THE INVENTION

The objective was substantially achieved, along with other desirable improvements, as evidenced by the following unique combination of characteristics that are outstanding in the new variety and that distinguish it from 'Nadorcott', as well as from all its derivatives of which I am aware. Among several selections, 'Star Cott 3' has several distinct characteristics that make it unique as compared to 'Nadorcott' including but not limited to:

1. Low viable pollen as shown by pollen culture on sucrose-Agar medium (8% for 'Star Cott 3' compared to more than 60% for 'Nadorcott').

2. Female sterility allowing production of seedless fruits (0.5 seeds per fruit for 'Star Cott 3' versus 13 seeds per fruit for 'Nadorcott') under heavy open field cross-pollination.
3. Maturity of 'Star Cott 3' is up to 2 weeks later than 'Nadorcott' in Beni Mellal, Morocco.
4. Compact canopy with a significant potential for high density planting (1666 plants/ha) for a swift achievement of significant yields and an accelerated return on investment.

'Star Cott 3' also has several distinct characteristics from 'Star Cott 1', including but not limited to:

1. 'Star Cott 1' has a phenotype of dense vegetation with numerous branches and abundant narrow long leaves, while 'Star Cott 3' is characterized by thinner vegetation with elongated branches and large leaves.
2. Early ripening time (weeks 48 to 52) for 'Star Cott 1' versus a later ripening time (weeks 4 to 9) for 'Star Cott 3' in the Beni Mellal region of Morocco.

Asexual reproduction of this new variety by bud-grafting, as performed in Kenitra, Morocco, shows that the foregoing and all other characteristics and distinctions come true to form and are established and transmitted through succeeding propagations. Bud-eyes are collected and side grafted on a certified receptive Volkamer lemon root-stock and grown for development under plastic house covered with a layer of anti-insect white screen and a top layer of anti-UV yellow plastic. Each of the progeny exhibits identical characteristics to the original plant. The present invention has not been evaluated under all possible environmental conditions. The phenotype may change with variations in environment without a change in the genotype of the plant.

BRIEF DESCRIPTION OF THE DRAWINGS

The accompanying illustrations show typical specimens of the tree, flowers, and fruit of 'Star Cott 3' depicted in color as nearly true as it is reasonably possible to make the same in a color illustration of this character.

'Star Cott 3' is indicated in photograph illustrations as 'Super Cott 3', which was the prior variety name of 'Star Cott 1'.

DETAILED BOTANICAL DESCRIPTION

The following is a detailed description of my new mandarin tree cultivar with color descriptions using terminology in accordance with The Royal Horticultural Society (London) Colour Chart, 4$^{th}$ Edition, (2001), except where ordinary dictionary significance of color is indicated. Observations were made of a 5-year old tree.

Figure 2:
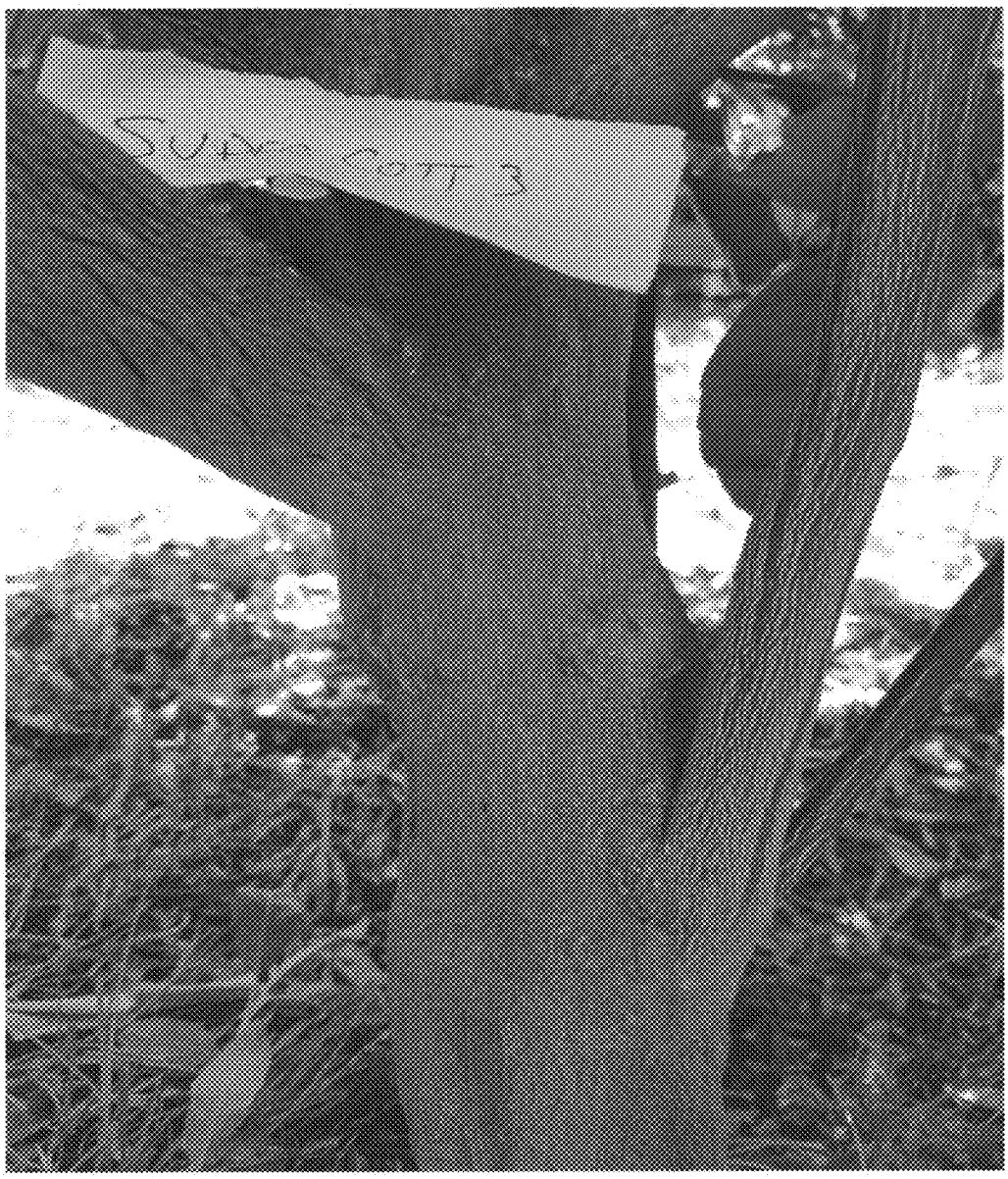
FIG. 2 is a photograph of 'Star Cott 3' trunk showing that the stem is strong with slightly rough bark. It has a diameter slightly less than the root-stock.

Tree:

*Plant diameter.*—230 cm on a 5 year old tree on *Citrus volkameriana* root-stock Trunk: stem is firm with a smooth bark; its diameter is equal to the root-stock. See FIG. 2.

Figure 1:
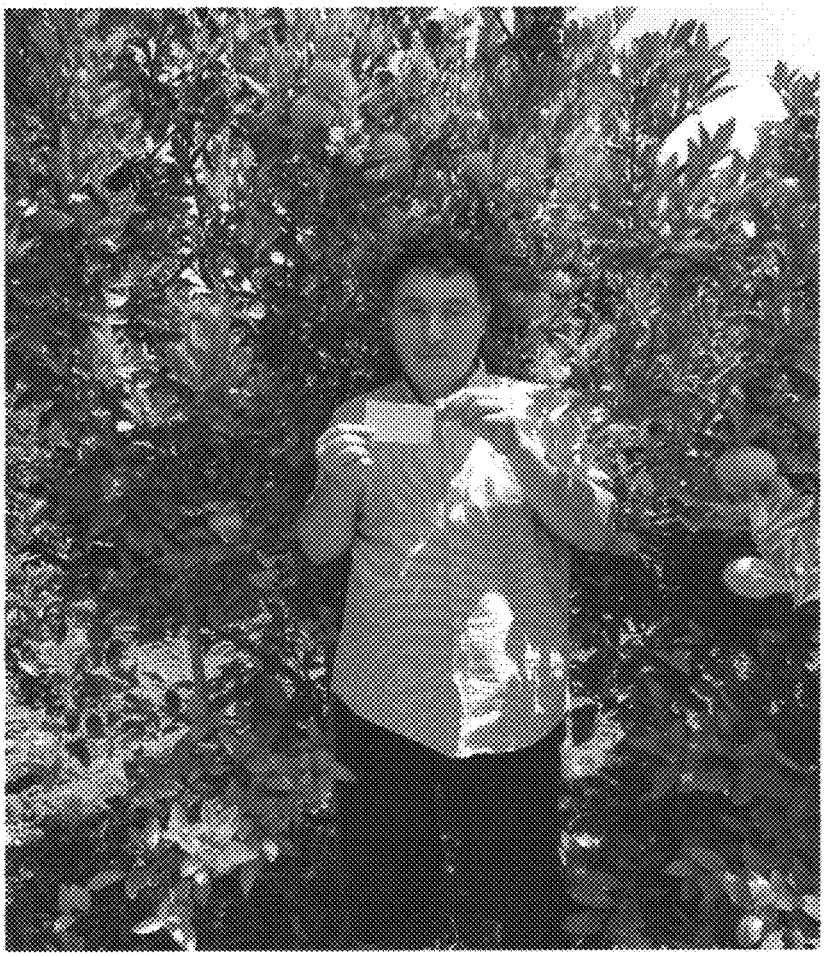
FIG. 1 is a photograph of 'Star Cott 3' tree with a compact canopy and an upright growth.

*Canopy.*—Vigorous vegetation with marked upright growth resulting in an ellipsoid shape. The density of branches is high; their attachment angle is narrow. See FIG. 1.

Figure 3:
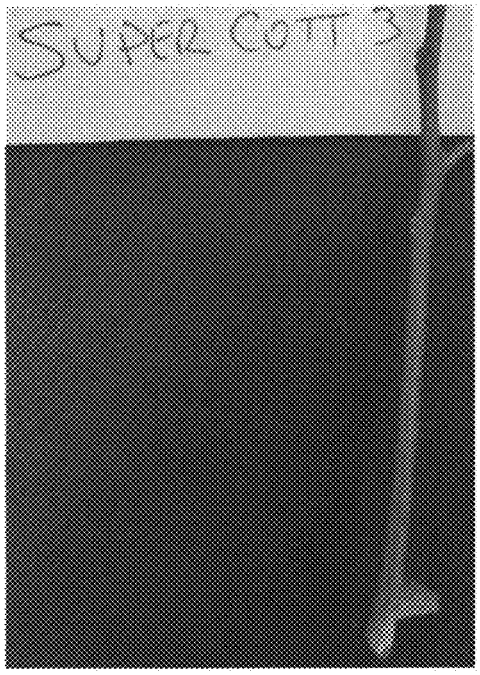
FIG. 3 is a photograph of a 'Star Cott 3' first year twig, which is green and glabrous.
Figure 4:
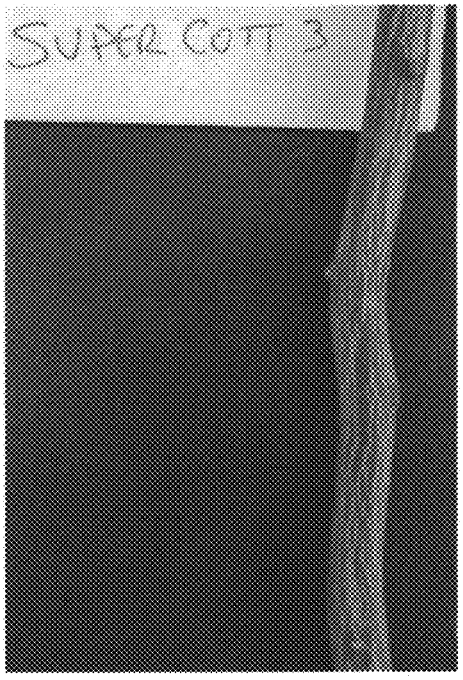
FIG. 4 is a photograph of a 'Star Cott 3' second year twig, which is striate.

*Twig.*—First year twig is glabrous, moderately thick and has a green color. See FIG. 3. It becomes subsequently striate with age. See FIG. 4. No thorns and no spines.

*Growth conditions.*—'Star Cott 3' is adapted to very high-density planting (1666 plants/ha) on trifoliate root-stocks and can achieve high yields starting from 3 years of age. No particular farming care techniques are needed to grow 'Star Cott 3'. It does not require any special conditions beside what is usually applied for 'Nadorcott'.

Stem description:

*Stem length.*—490 mm.
*Diameter.*—108 mm.
*Texture.*—Smooth.
*Strength.*—Strong.
*Color.*—RHS N 199 B dark gray.

Figure 5:
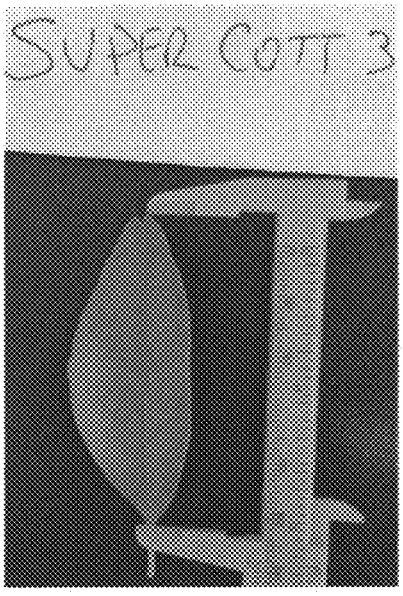
FIG. 5 is a photograph of a 'Star Cott 3' leaf, showing ovate and slightly crenate shape.
Figure 6:
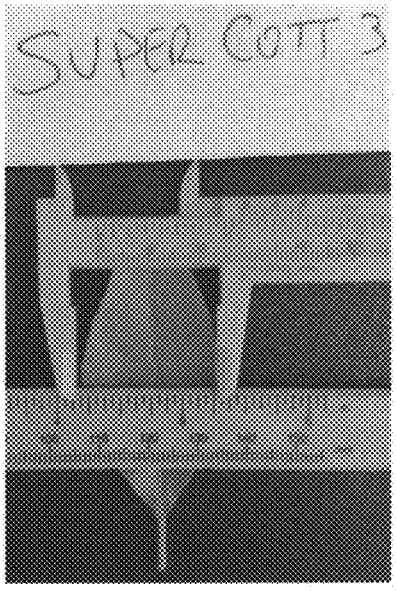
FIG. 6 is a photograph of a 'Star Cott 3' leaf, showing apex slightly emarginated.
Figure 7:
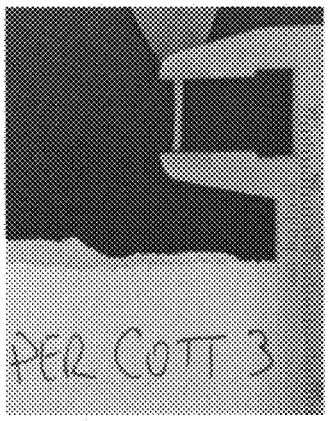
FIG. 7 is a photograph of a 'Star Cott 3' petiole, showing it is glabrous with no wings.
Figure 8:
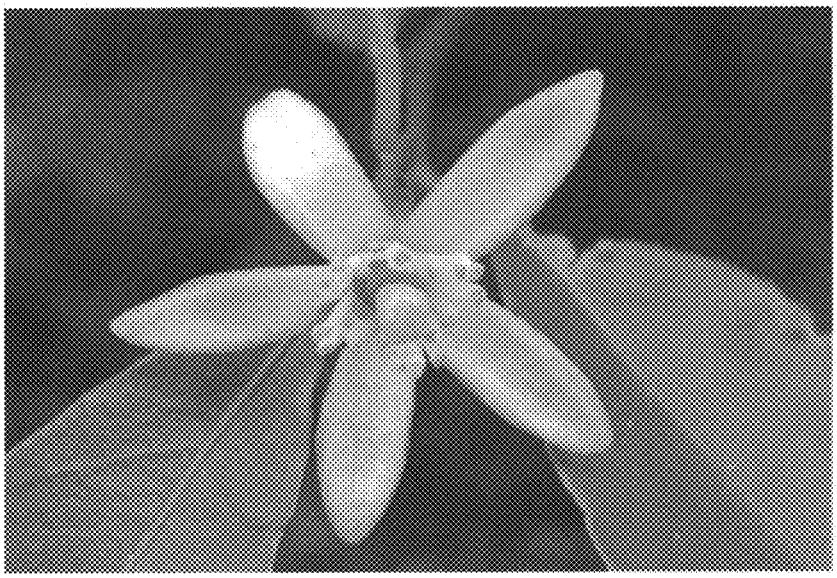
FIG. 8 is a photograph of a 'Star Cott 3' flower with five petals and 16 to 20 stamens.
Figure 9:
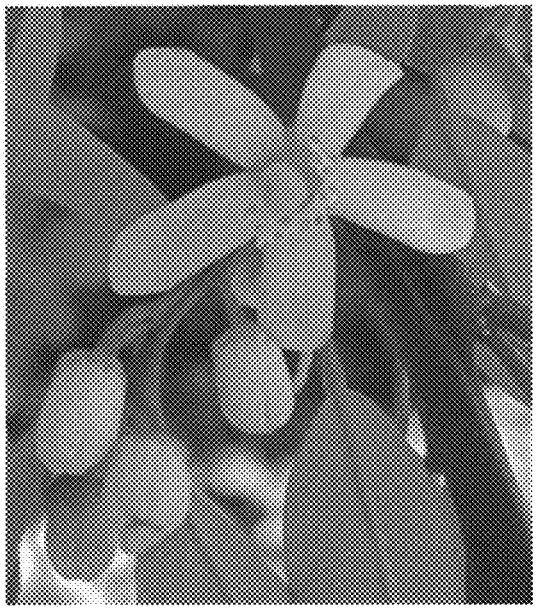
FIG. 9 is a photograph of 'Star Cott 3' young flowers before anthesis.
Figure 10:
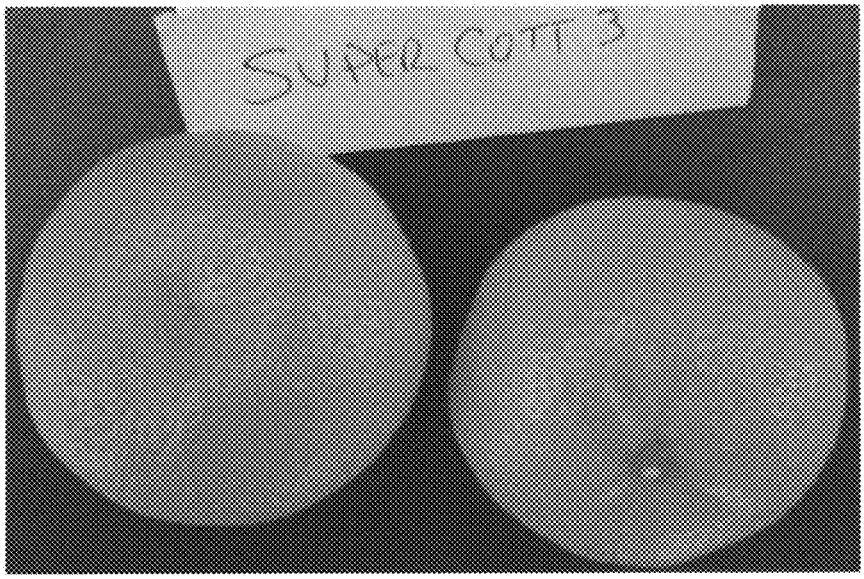
FIG. 10 is a photograph of a 'Star Cott 3' fruit, having a width of about 65 to 67 mm, with an areola that is sometimes obvious and stylar rudimentary scar.
Figure 11:
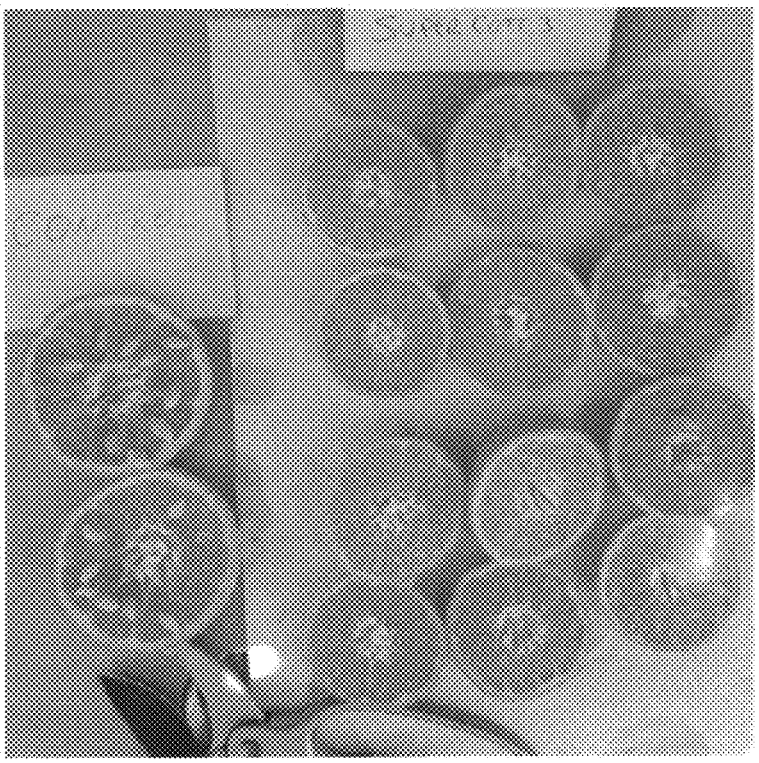
FIG. 11 is a photograph comparing 'Star Cott 3' cut fruits (with 0.5 seeds and 9 to 11 segments) and 'Nadorcott' cut fruits (16 seeds with 9 to 11 segments).
Figure 12:
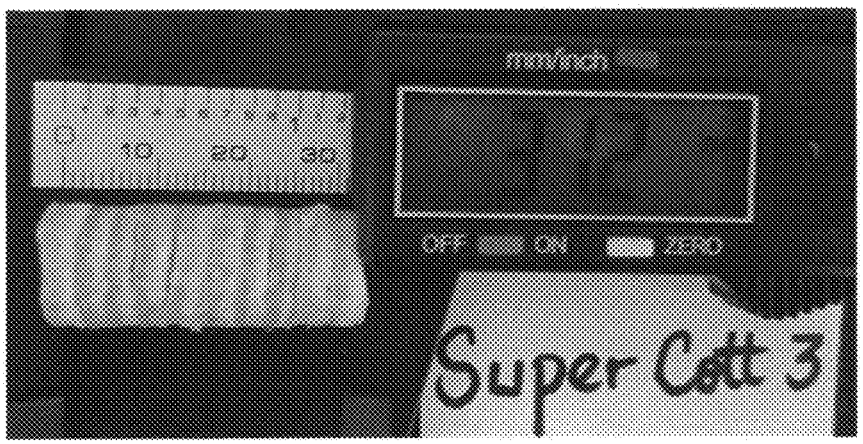
FIG. 12 is a photograph of a 'Star Cott 3' fruit peel, with a thickness of 3.12 mm.
Figure 13:
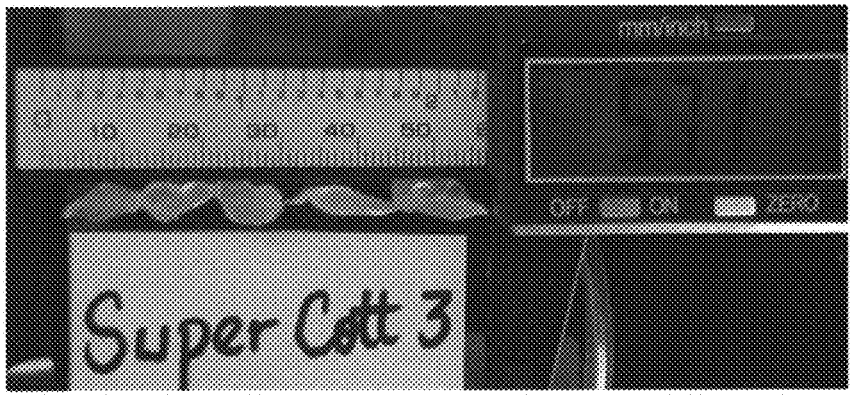
FIG. 13 is a photograph of a 'Star Cott 3' fruit juice bag length of 11.42 mm.
Figure 14:
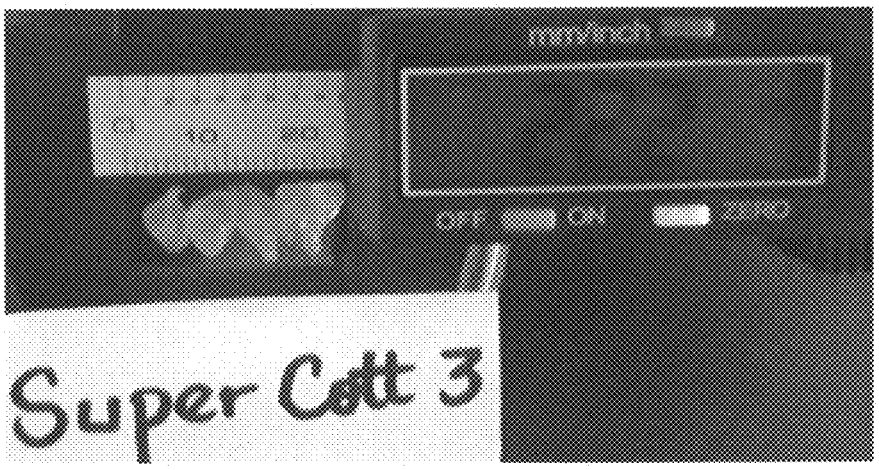
FIG. 14 is a photograph of a 'Star Cott 3' fruit juice bag width of 4.44 mm.
Figure 15:
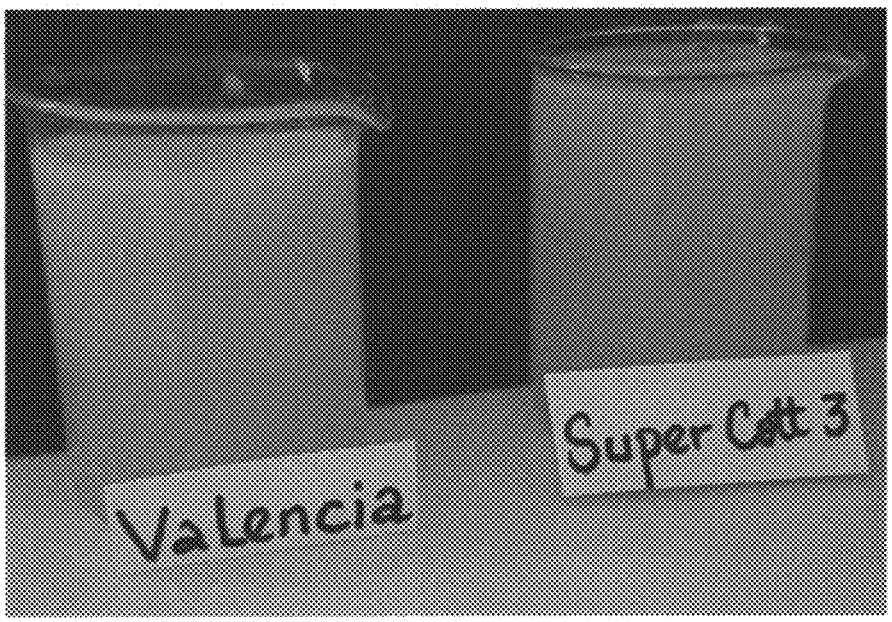
FIG. 15 is a photograph comparing juice extract from late Valencia and 'Star Cott 3' fruit.
Figure 16:
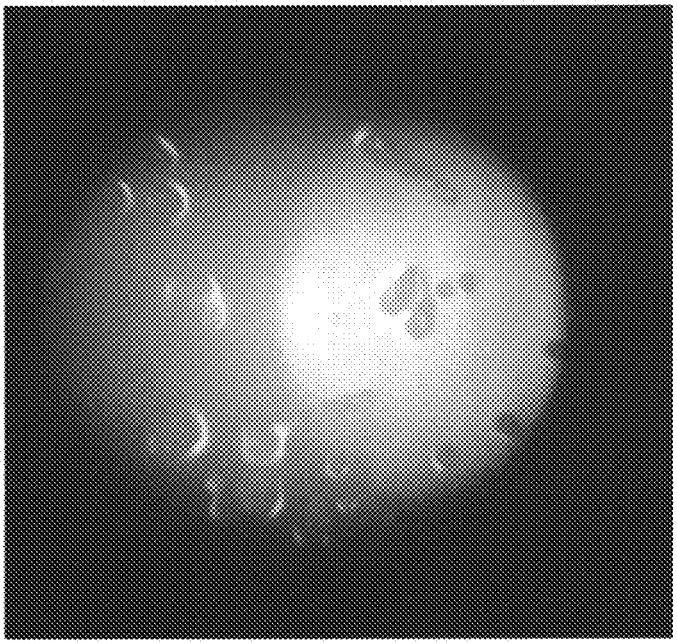
FIG. 16 is a photograph of microscopic view of pollen germination test on agar/sucrose medium for 'Star Cott 3'. Count revealed a germination rate of 8% for 'Star Cott 3' compared to more than 60% for 'Nadorcott'.

Leaf description: Unifoliate with an entire margin, it is elliptic in shape and moderately conduplicate with a glabrous non-winged petiole. The lamina has an obtuse apex slightly emarginated. See FIGS. 5-6.

*Shape.*—elliptic.
*Length.*—58 mm.
*Width.*—28 mm.
*Apex.*—Obtuse with slight emargination.
*Margin.*—Entire.
*Texture (both surfaces).*—Glabrous.
*Color.*—Adaxial: RHS 132 C (moderate Green); Abaxial: RHS 132 D (light Green).
*Petiolate of sessile.*—Petiolate. Petiolate length: 7 mm. Petiolate diameter: 0.8 mm. Petiolate color: RHS 139 D (moderate Yellow Green).

Root description: Grafted on *Citrus volkameriana* rootstock.

Flowers: Single type of flowers in clusters and single flowers at the tip of a leafy bud. Like 'Nadorcott', 'Star Cott 3' flowers in mid-March with abundant flowering.

*Height.*—12.5 mm.

*Diameter.*—7.1 mm before anthesis.

*Typical date of bloom.*—Mid-March in Beni Mellal, Morocco.

*Number of flowers.*—1 type in singles and clusters.

*Color.*—RHS 155 D (Yellowish White.)

*Pedicel.*—8 to 10 mm in length.

*Calyx.*—5 mm in diameter with 5 sepals arranged in a cup-like structure. Each sepal has an isosceles triangular shape measuring 3.5 mm at the base and 2.5 mm on the side.

*Corolla.*—Composed of 5 petals (14.5 mm in length and 5.0 mm in width) arranged in a circle in alternation with the sepals.

*Stamens.*—About 20 in number that stick together, arranged in a circle around the pistil and their anthers are positioned around the stigma at about the same height.

Rostellum:

*Length.*—9.2 mm.

*Thickness.*—1.2 mm.

*Color.*—RHS 162 A (moderate Yellow).

Fruit: Fruit attachment to the stalk is strong with sometimes short radial grooves which are not always conspicuous. No neck is present.

*Shape.*—Slightly larger than longer and has an obloid form.

*Diameter at equatorial level.*—65 mm and it is truncate at both stalk and distal ends.

*Width.*—65 to 67 mm.

*Texture.*—Smooth.

*Color.*—Green fruit — RHS 126 A (medium blue Green); non-dehiscent fruit — RHS 32 C (slightly reddish-Orange).

*Fruit rind.*—Slightly reddish-Orange in color — RHS 32C, and has a thickness of about 2.95 mm shared equally by flavedo and albedo. The rind is dotted with oil glands of about 1 mm in diameter at a density of 30 about per $cm^2$, and about twice as much tiny oil glands (about $60/cm^2$). The albedo is of pinkish White color RHS N155B.

*Segments.*—9 to 11 which are uniform with a thin but firm membrane.

*Seeds.*—Mean seed count under high cross pollination pressure in mixed bloc with 'Nadorcott', Rough Lemon and Clementine in adjacent rows was 0.5 per fruit. Seeds are polyembryonic and seed coat is of yellowish-White color (RHS 155 D).

*Fruit axis.*—Hollow with a diameter of about 8 mm.

*Peel thickness.*—3.12 mm. A small stylar scar is visible and a distinct areola is visible on some fruits. No navel is visible when the fruit is peeled.

*Pulp.*—Slight reddish orange color RHS N25B, it is soft and juicy. Juice vesicles are delicate rolls of 8.5 mm long and 3 mm large. The percentage of juice in the endocarp exceeds 50%, Total Soluble Solids (TSS) varies from 10 to 13% and Titratable Acidity (TA) varies between 13 to 0.75% depending on the maturity stage.

Production: 5-year old planting with a spacing of 6 by 2 m produces over 50 metric tons per ha.

Tolerance to heat wave: 'Star Cott 3' is similar to the mother variety 'Nadorcott', which is relatively tolerant to mid-spring heat waves that occur in the Mediterranean Basin.

Tolerance to frost: 'Star Cott 3' is similar to the mother variety 'Nadorcott', which is resistant to mild negative temperatures (0 to −3° C.) if the duration does not exceed 1 to 2 hours. If this range of negative temperatures is recorded for several consecutive days, or if temperatures decline below −3° C., the fruit is affected by reduction of juice content and irreversible skin damage, especially fruits of the outer side of the canopy.

Disease resistance: No trials have been conducted, however, 'Star Cott 3' does not seem to be sensitive to *Alternaria*.

Market use: Fruit of 'Star Cott 3' is intended mainly for fresh fruit consumption, as it is the case for the product of 'Nadorcott' which is commercialized worldwide.

I claim:

1. A new and distinct mandarin tree, named 'Star Cott 3', as herein shown and described.

* * * * *